United States Patent [19]

Mark et al.

[11] 4,320,234

[45] Mar. 16, 1982

[54] PROCESS FOR PURIFYING CRUDE DIPHENOLS

[75] Inventors: Victor Mark, Evansville; Charles V. Hedges, Mt. Vernon, both of Ind.

[73] Assignee: General Electric Company, Mt. Vernon, Ind.

[21] Appl. No.: 156,953

[22] Filed: Jun. 6, 1980

Related U.S. Application Data

[63] Continuation of Ser. No. 41,641, May 23, 1979, abandoned, which is a continuation-in-part of Ser. No. 755,982, Dec. 30, 1976, abandoned.

[30] Foreign Application Priority Data

Dec. 29, 1977 [DE]  Fed. Rep. of Germany ....... 2758565
Dec. 28, 1977 [FR]  France ................................. 77 39515
Dec. 28, 1977 [JP]  Japan ................................ 52/157557
Dec. 29, 1977 [NL]  Netherlands ............................ 14564

[51] Int. Cl.³ .......................................... C07C 39/16
[52] U.S. Cl. .................................................. 568/724
[58] Field of Search ........................................ 568/724

[56] References Cited

U.S. PATENT DOCUMENTS

| | | | |
|---|---|---|---|
| 2,959,622 | 11/1960 | Grimme et al. | 568/724 |
| 3,277,183 | 10/1966 | Heller et al. | 568/724 |
| 3,919,330 | 11/1975 | Kwantes et al. | 568/724 |
| 4,242,527 | 12/1980 | Mark et al. | 568/724 |

OTHER PUBLICATIONS

Vogel, "Practical Organic Chemistry", 3rd ed. (1957), pp. 122–128.

*Primary Examiner*—Joseph E. Evans
*Attorney, Agent, or Firm*—Martin B. Barancik; William F. Mufatti

[57] ABSTRACT

A process for purifying crude diphenols via a water co-solvent system is disclosed.

4 Claims, No Drawings

PROCESS FOR PURIFYING CRUDE DIPHENOLS

This is a continuation of application Ser. No. 41,641, filed May 23, 1979 now abandoned which in turn, is a continuation-in-part of application Ser. No. 755,982 filed Dec. 30, 1976, now abandoned.

BACKGROUND OF THE INVENTION

It is well known that the purity of diphenols is of paramount importance regarding the quality of polymers which are prepared therefrom. Isomeric diphenols and other impurities specified herein that often accompany the desired p,p'-diphenols are often deleterious since such impurities do not participate as well in and may impede the polymerization processes. It is thus desirable and important to obtain the p,p'-diphenols in their highest purity in order to secure the quality of the polymers which are prepared therefrom. Since isomeric diphenols always accompany the desired p,p'-diphenols, purification of the crude reaction products is always necessary.

Purification of crude mixtures of p,p'-diphenols is often effected by the use of organic solvents such as benzene, methylene chloride or toluene. The use of these and similar solvents results in costly purification due to both the cost of solvents and the relative inefficiency of the method. Another purification method is set forth in U.S. Pat. No. 3,919,330. In this method crude 2,2-bis(4-hydroxyphenyl)propane is dissolved in ethylene glycol and the 2,2-bis(4-hydroxyphenyl)propane is recovered after partial precipitation with water. However, this method requires the use of large amounts of ethylene glycol and the necessity of an additional step of recovering the anhydrous glycol from the aqueous mother liquor in order to reuse it. Furthermore, although this process teaches a method of separating the desired 2,2-bis(4-hydroxyphenyl)propane from its more soluble isomer, it does not effect removal of the less soluble impurities from the crude product.

DESCRIPTION OF THE INVENTION

It has been found that p,p'-diphenols of high purity can be obtained by the steps of: (a) dispersing the crude p,p'-diphenol in a heated system of water and an alcoholic co-solvent or mixtures of co-solvents so that the desired p,p'-diphenol and the impurities that are more soluble than the desired diphenol are dissolved in the system at a temperature that is at or near the boiling point of water or the water/co-solvent system; (b) removing those impurities that are less soluble than the desired diphenol from the system, such as by filtration; and (c) cooling the system to achieve the separation of the desired purified diphenol. The "more soluble" impurities will remain in the aqueous-co-solvent system.

For example, one method to achieve this purification comprises dispersing the crude p,p'-diphenol in water, heating the resulting slurry and then adding a water soluble alcoholic co-solvent until the near dissolution of the crude diphenol results, at or near the boiling point of the resulting solvent system. Subsequent filtration of the less soluble impurities, cooling the filtrate and recovery of the recrystallized solids yields p,p'-diphenols of improved purity (assay).

Alternatively, the crude diphenols are heated with a premixed water and co-solvent mixture, with stirring, until near dissolution of the crude diphenol results, followed by filtration of the less soluble impurities, cooling the filtrate and subsequent recovery of the recrystallized solid purified p,p'-diphenol.

The term "near dissolution", as used herein, refers to the dissolution of the desired p,p'-diphenol and any impurities that are more soluble (in the water/co-solvent system) than the desired p,p'-diphenol, leaving undissolved those impurities that are less soluble, in the water/co-solvent system, than the desired diphenol. Depending on the needs of the individual practitioner of this invention, such as the particular p,p'-diphenol which is to be purified, the desired degree of purification of the p,p'-diphenol and considerations such as of both time and expense, it is understood that such a skilled practitioner may choose to have less than 100% of the desired p,p'-diphenol dissolved in the water/co-solvent system.

The term "alcoholic co-solvents" as used herein refers to di-, tri- or polyhydroxylic alcohols, ether-alcohols, aminoalcohols, ketoalcohols, and the like. Examples of these water soluble alcoholic co-solvents include 1,2-ethanediol, 1,2-propanediol, 1,3-propaneidol, 1,2,3-propanetriol. 1,2-butanediol, 1,3-butanediol, 1,4-butanediol, diethanolamine, triethanolamine, diethyleneglycol, triethyleneglycol, dipropyleneglycol, thiodiethanol, etc. and mixtures thereof. Also, one or more of these alcoholic co-solvents and water may be employed concurrently to accomplish recrystallization.

The amount of water soluble alcoholic co-solvent employed herein is dependent upon the amount of water used in the recrystallization, in that the larger the amount of water per solute, the greater the amount of co-solvent that will be required.

Generally, after completion of the addition of the alcoholic co-solvent to the slurry of water-crude p,p'-diphenol, the weight ratio of co-solvent to the water-crude p,p'-diphenol is from about 10:100 to about 40:100.

A wide variety of diphenols may be purified according to the method of the instant invention. The preferred diphenols include 2,2-bis(4-hydroxyphenyl)propane, 4,4'-thiodiphenol, 4,4'-oxydiphenol, cyclohexylidenediphenol; p,p'-bisphenol, 2,2-bis (3,5-dimethyl-4-hydroxyphenyl)propane, as well as the corresponding tetrachloro and tetrabromo analogs, p,p'-sulfonyldiphenol, bis(3,5-dimethyl-4-hydroxyphenyl sulfone), and the like. The preferred diphenol, 2,2-bis(4-hydroxyphenyl)propane consists, in its crude state, of a mixture of the p,p' and o,p' isomers and a host of other impurities. Some of these impurities, such as the o,p' isomer, are more soluble than the p,p' isomer in the water/co-solvent system and some are less so. It is, therefore, a feature of this invention to add to the aqueous slurry of the crude reaction mixtures just enough co-solvent that is necessary for the dissolution of the o,p' and p,p' isomer content of the mixture, leaving the lesser soluble components undissolved. The latter are conveniently removed by filtration. Subsequent cooling of the filtered solution deposits the less soluble p,p' isomer, leaving much or all of the more soluble o,p' isomer and other more soluble components in solution.

The term "more soluble impurities" are used in the specification and claims refers to those impurities that are more soluble, in the water/co-solvent system, that the desired p,p'-diphenol. The term "less soluble impurities" as used in the specification and claims refers to those impurities that are less soluble, in the water/co-solvent system, than the desired p,p'diphenol.

The temperature at which the instant purification method is conducted should be above ambient. The maximum temperature is not critical, although sometimes it is determined by the boiling point of the lowest boiling co-solvent. When working at atmospheric pressure, it is desirable to stay near about 90° C. to 100° C., so that the solvent properties of water can be best utilized. Since the solubility of diphenols increases dramatically with temperature, it is often advantageous to use super-atmospheric pressure, such as those obtained by pressurizing the recrystallization vessels by inert gases or by employing autogeneous pressures. In some cases, 150° C. or even higher temperatures are preferable, such as those available by the use of superheated steam.

It was found that the use of aqueous solvents results usually in the formation of well developed larger crystals of the desired purified product, which can be readily separated by filtration. In the case of 2,2-bis(4-hydroxyphenyl)propane, the crystals have the rhombic crystal structure which may have on their surfaces a contamination of the more isomeric impurities, usually the o,p' isomer. A simple slurrying or rinsing of these crystals by a proper solvent, such as methylene chloride, readily removes the impurities and leaves behind the rhombic crystals of the pure p,p' isomers. Similar situations exist with a number of analogous diphenols.

DESCRIPTION OF THE PREFERRED EMBODIMENT

The following examples are set forth to illustrate more clearly the invention to those skilled in the art. Unless otherwise specified, where parts or percents are mentioned, they are parts or percents by weight.

EXAMPLE I

To a one-liter, three-necked flask, equipped with a stirrer, reflux condenser, addition funnel and thermometer, there was charged 50 grams of crude, technical 2,2-bis(4-hydroxyphenyl)propane (bisphenol-A) and 500 ml. of water and the resultant slurry was heated with the aid of a heating mantle. When the water started to reflux, pure, anhydrous 1,2-ethanediol (ethyleneglycol) was gradually added to the aqueous heterogeneous liquid while maintaining a gentle reflux. It required 137.5 grams of the co-solvent glycol to dissolve the desired diphenol isomer and the more soluble impurities. The less soluble impurities were filtered from the system. Upon cooling to ambient temperatures, well developed rhomboid crystals of p,p'-bisphenol-A separated out, and were isolated by filtration. The recrystallized product, that was obtained in 99% recovery, contained 96% of p,p'- and 1.8% of o,o'-isomer, whereas the starting material contained 93.1% and 3.4%, respectively, of the two isomers.

EXAMPLES II to VIII

The procedure of Example I was repeated exactly, except that 1,2-ethanediol was replaced with the co-solvents and in the amounts shown in Table I.

TABLE I

Co-Solvents Required to Dissolve the p,p' and o,p' Isomers Present in 50 Grams of Crude Bisphenol-A in 500 Grams of water at 100° C.

| Example | Co-solvent | Amount of Co-solvent (grams) |
|---|---|---|
| II | 1,2-ethanediol | 137.5 |
| III | 1,2-propanediol | 98.9 |
| IV | 1,3-butanediol | 91.0 |
| V | 1,4-butanediol | 96.5 |

TABLE I-continued

Co-Solvents Required to Dissolve the p,p' and o,p' Isomers Present in 50 Grams of Crude Bisphenol-A in 500 Grams of water at 100° C.

| Example | Co-solvent | Amount of Co-solvent (grams) |
|---|---|---|
| VI | thiodiethylene glycol | 142.6 |
| VII | tripropylene glycol | 189.0 |
| VIII | glycerine | 226.0 |

EXAMPLES IX to XII

The procedure of Example I was exactly repeated except that the diphenols shown in Table II were used in place of bisphenol-A.

TABLE II

| Example | | 1,2-Ethanediol (grams) |
|---|---|---|
| IX | 4,4'-thiodiphenol | 33.5 |
| X | 4,4'-cyclohexylidene diphenol | 494.2 |
| XI | 2,2'-bis(3-chloro-4-hydroxyphenyl)propane | 385.0 |
| XII | bis(3,4-dimethyl-4-hydroxyphenyl)sulfone | 480.0 |

COMPARATIVE EXAMPLE

A crude BPA composition was divided into two lots. Lot A was purified, using an ethylene glycol/water system, by the process as generally set forth in U.S. Pat. No. 3,919,330, Illustrative Embodiment II thereof, while Lot B was purified as per the process of Example I above. Table III sets forth the composition of the crude BPA and the composition of the products purified by the process of U.S. Pat. No. 3,919,330 and the claimed process.

TABLE III

| Component | Crude BPA (Wt. %) | Purified Lot A (Wt. %) | Purified Lot B (Wt. %) |
|---|---|---|---|
| p,p'-BPA[a] | 96.927 | 98.231 | 99:500 |
| Chroman-I[b] | 0.318 | 0.318 | 0.137 |
| Spirodiphenol[c] | 2.192 | 1.345 | 0.257 |
| IPP-linear dimer[d] | 0.563 | 0.106 | 0.106 |

[a]2,2-bis(4-hydroxyphenyl)propane
[b]p-2,2,4-trimethyl-4-chromanyl)phenol
[c]6,6'-dihydroxy-3,3,3',3'-tetramethyl-1,1'-spirobiindane
[d]4-methyl-2,4-bis(p-hydroxyphenyl)-1-pentene (isopropenylphenol linear dimer)

Obviously, other modifications and variations of the present invention are possible in the light of the above teachings. It is therefore to be understood that changes may be made in the particular embodiments of the invention described which are within the full intended scope of the invention.

What is claimed is:

1. A process for purifying crude diphenol, said crude diphenol comprising 2,2-bis(4-hydroxyphenyl) propane and impurities which are more soluble than the 2,2-bis(4-hydroxyphenyl) propane and impurities which are less soluble than the 2,2-bis(4-hydroxyphenyl) propane in a water polyhydroxylic alcohol solvent system to recover the purified 2,2-bis(4-hydroxyphenyl) propane which comprises (a) dispersing the crude, untreated diphenol in a solvent system consisting of water and a polyhydroxylic alcoholic co-solvent or mixture of co-solvents at a temperature of from about 90° to about 100° C., measured at atmospheric pressure, until near dissolution of said crude diphenol results and the 2,2- bis(4-hydroxyphenyl) propane and the more soluble impurities are dissolved in said solvent system, the weight ratio of said co-solvent or said mixture of co-solvents to said water plus crude diphenol being in the range of about 10–40:100;

(b) removing the less soluble impurities from the solvent system; and (c) cooling the solvent system to a temperature wherein the purified 2,2-bis(4-hydroxyphenyl) propane is separated from the more soluble impurities.

2. A process according to claim 1 wherein step (a) is carried out at super-atmospheric pressure.

3. A process for purifying crude diphenol, said crude diphenol comprising 2,2-bis(4-hydroxyphenyl) propane and impurities which are more soluble than the 2,2-bis(4-hydroxyphenyl) propane and impurities which are less soluble than the 2,2-bis(4-hydroxyphenyl) propane in a water polyhydroxylic alcohol solvent system to recover the 2,2-bis(4-hydroxyphenyl) propane which comprises (a) dispersing crude untreated diphenol in water;

(b) heating the resulting slurry;

(c) adding a polyhydroxylic alcoholic co-solvent or mixture of co-solvents to the slurry and continuing the dispersion of said crude diphenol in said slurry at a temperature of from about 90° to 100° C., measured at atmospheric pressure, until the near dissolution of said crude diphenol results and the 2,2-bis(4-hydroxyphenyl) propane and the more soluble impurities are dissolved in the resulting water co-solvent system, the weight ratio of said co-solvent or said mixture of co-solvents to said water plus crude diphenol being in the range of 10–40:100;

(d) removing the less soluble impurities from the solvent system; and (e) cooling the solvent system to a temperature wherein the purified 2,2-bis(4-hydroxyphenyl) propane is separated from the more soluble impurities.

4. A process according to claim 3 wherein step (c) is carried out at super-atmospheric pressure.

* * * * *

UNITED STATES PATENT AND TRADEMARK OFFICE
CERTIFICATE OF CORRECTION

PATENT NO. : 4,320,234
DATED : March 16, 1982
INVENTOR(S) : Victor Mark et al.

It is certified that error appears in the above—identified patent and that said Letters Patent is hereby corrected as shown below:

The term of this patent subsequent to December 30, 1997 has been disclaimed.

Signed and Sealed this

Eleventh Day of May 1982

[SEAL]

Attest:

GERALD J. MOSSINGHOFF

*Attesting Officer*  *Commissioner of Patents and Trademarks*